(12) United States Patent
Palumbo et al.

(10) Patent No.: US 6,508,794 B1
(45) Date of Patent: Jan. 21, 2003

(54) METHOD FOR COLLECTING AND DISPOSING OF HUMAN WASTE

(75) Inventors: Gianfranco Palumbo, Bad Homburg (DE); Vincenzo D'Acchioli, Kelkheim/Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,184

(22) PCT Filed: Jun. 26, 1998

(86) PCT No.: PCT/US98/13288

§ 371 (c)(1),
(2), (4) Date: Mar. 7, 2001

(87) PCT Pub. No.: WO00/00112

PCT Pub. Date: Jan. 6, 2000

(51) Int. Cl.[7] ............................................. A61F 13/15
(52) U.S. Cl. ................. 604/317; 604/321; 604/329; 604/339; 604/344; 604/349
(58) Field of Search ................. 604/317–349, 604/354, 355; 2/400–406

(56) References Cited

U.S. PATENT DOCUMENTS

| | | | | | |
|---|---|---|---|---|---|
| 3,292,626 A | * | 12/1966 | Schneider | ............. | 604/346 |
| 3,532,093 A | * | 10/1970 | Lovret | ............. | 604/346 |
| 4,453,938 A | * | 6/1984 | Brendling | ............. | 604/346 |

* cited by examiner

Primary Examiner—Jeanette Chapman
(74) Attorney, Agent, or Firm—Erich D. Hemm

(57) ABSTRACT

A method for collecting and disposing of urine and fecal excrement from an individual. The method is the simultaneous and independent use of a disposable urine management device and a disposable fecal management device. The disposable urine management device is independently applied in a releasable manner to the uro-genital area of the individual while the disposable fecal management device is independently applied in a releasable manner to the perineal area of the individual.

12 Claims, 8 Drawing Sheets

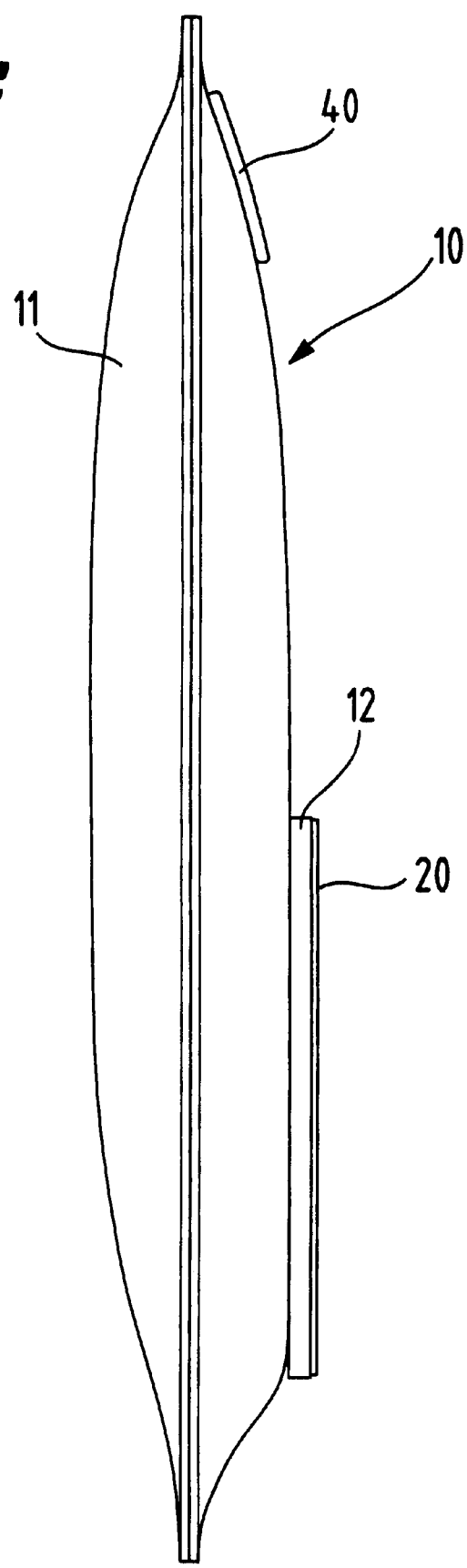

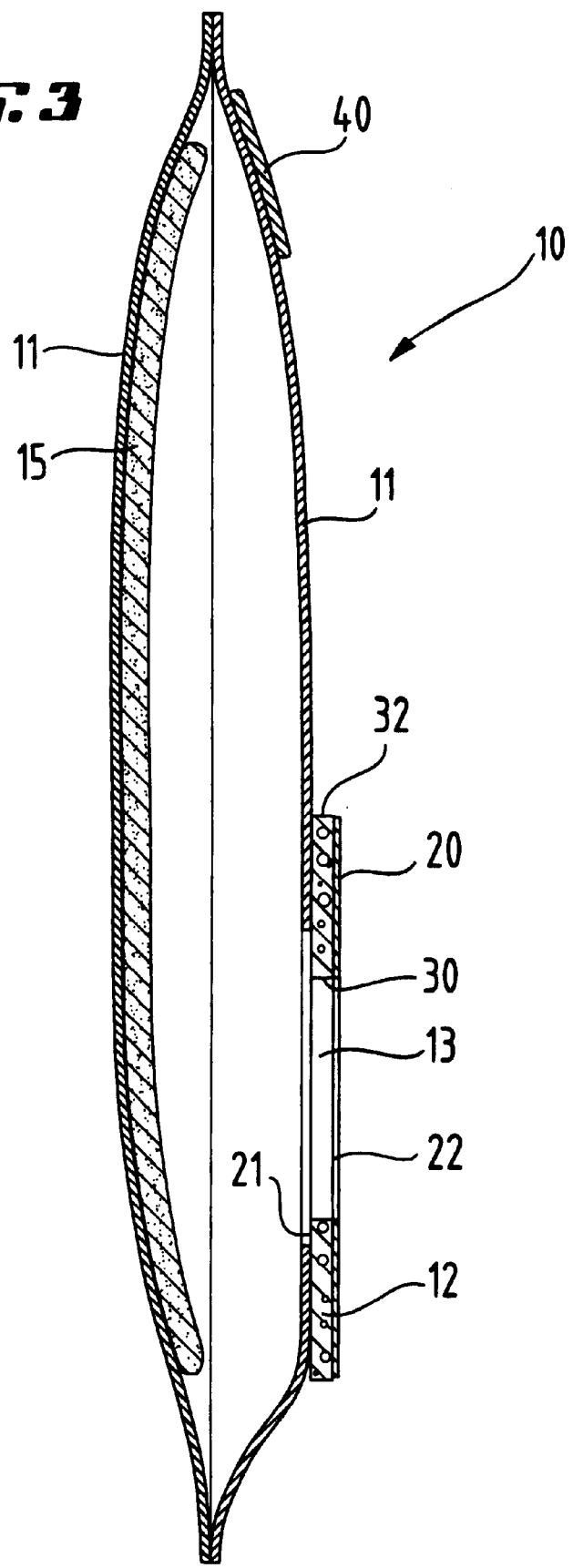

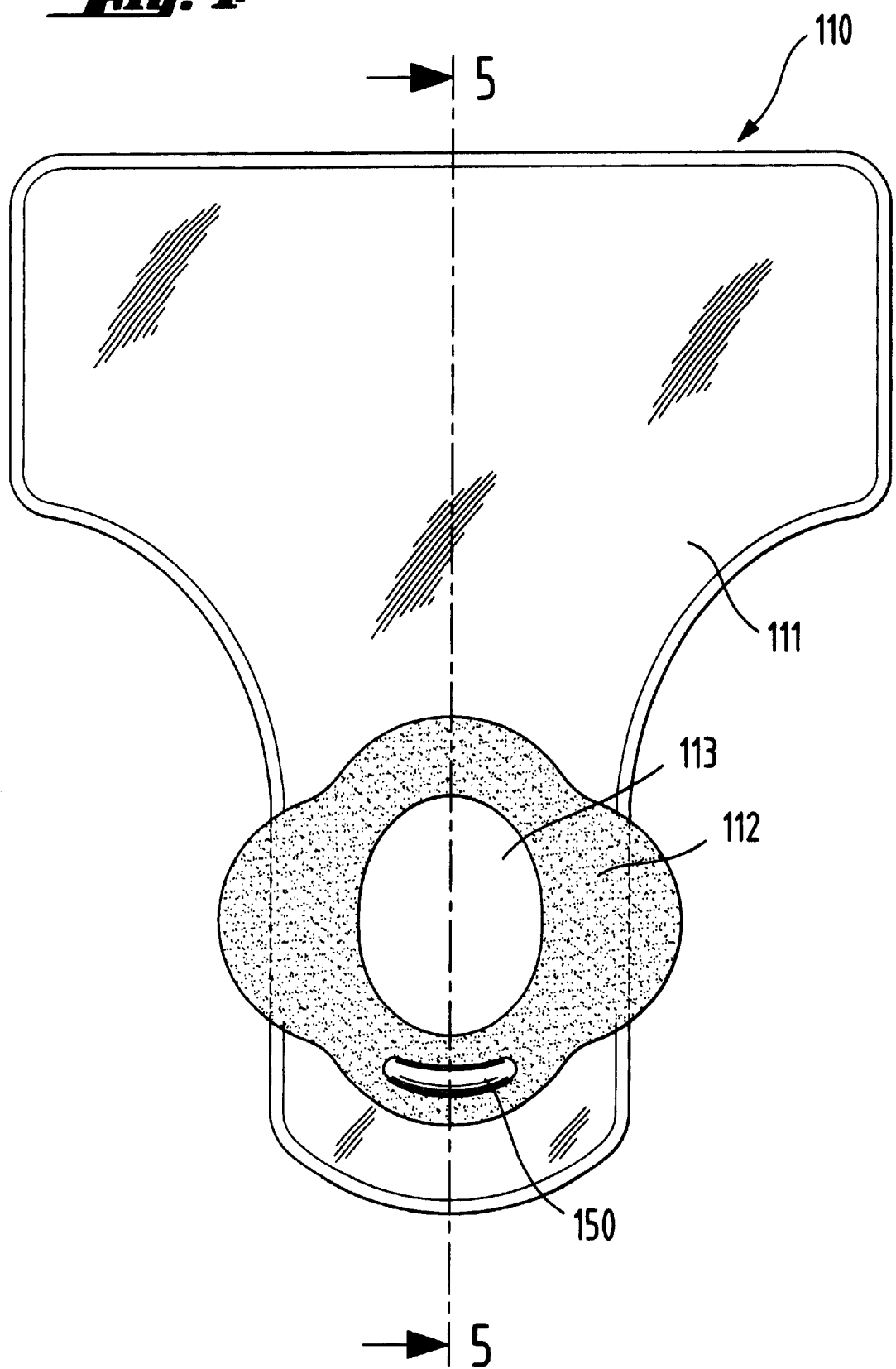

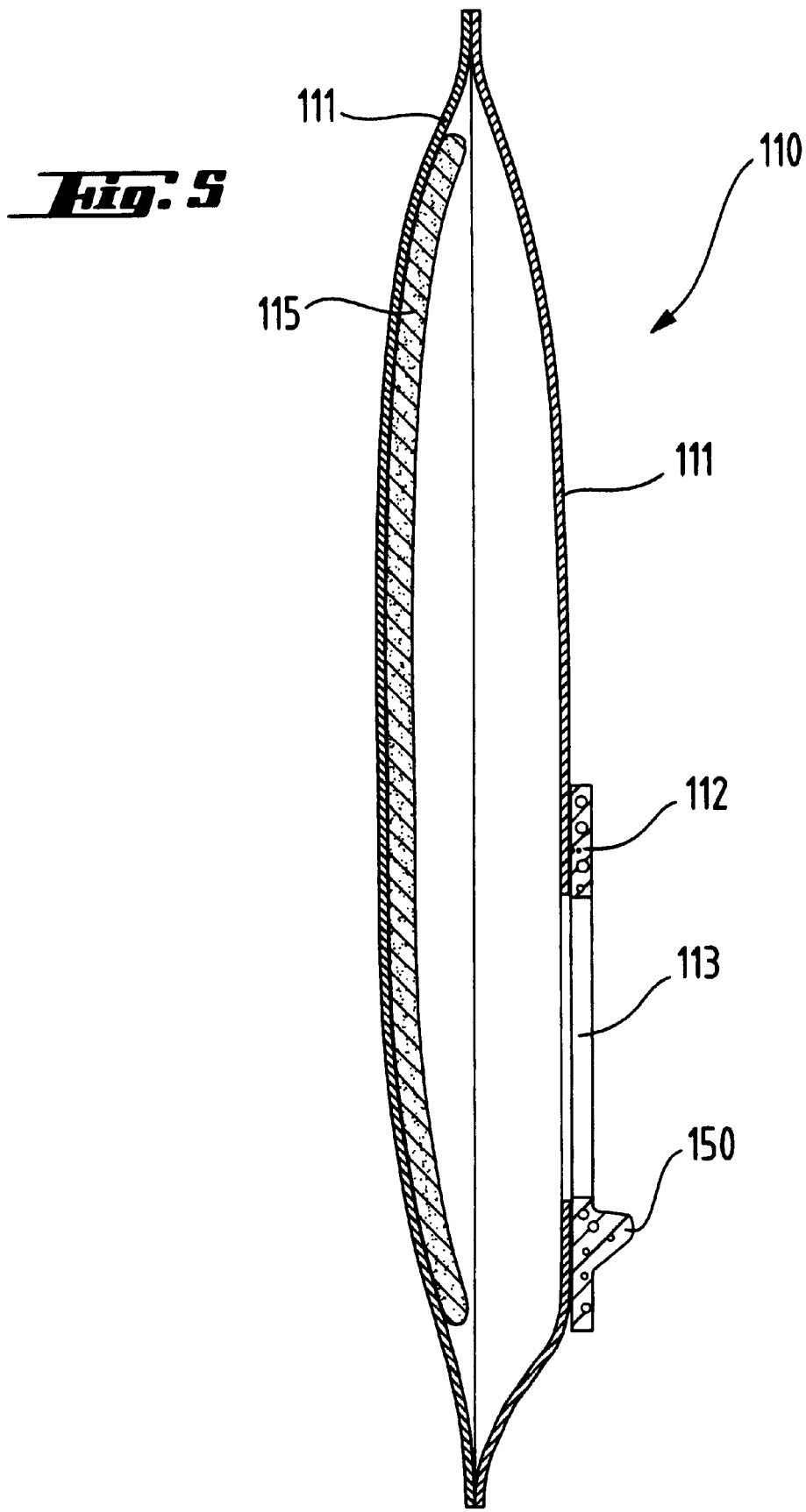

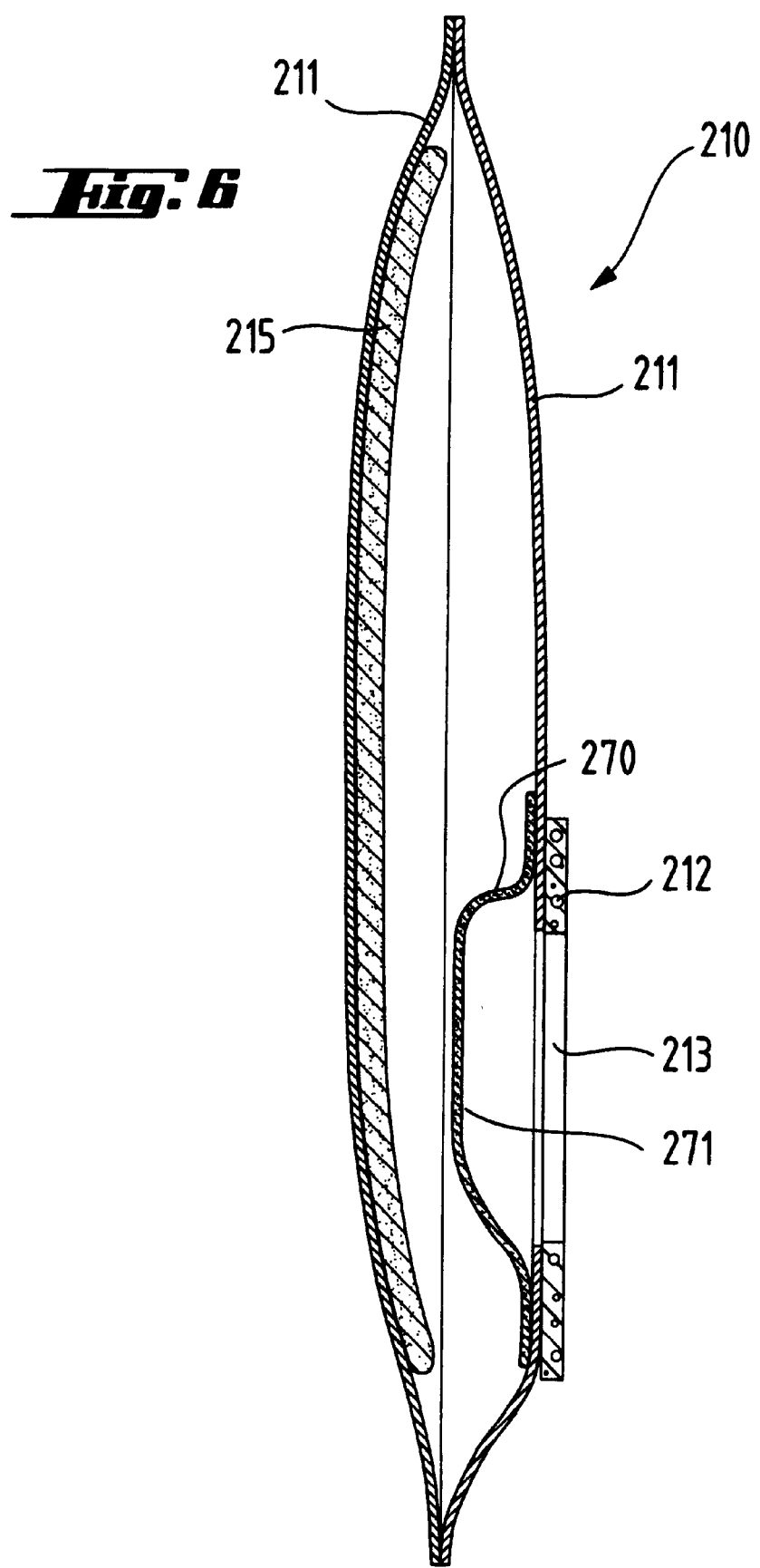

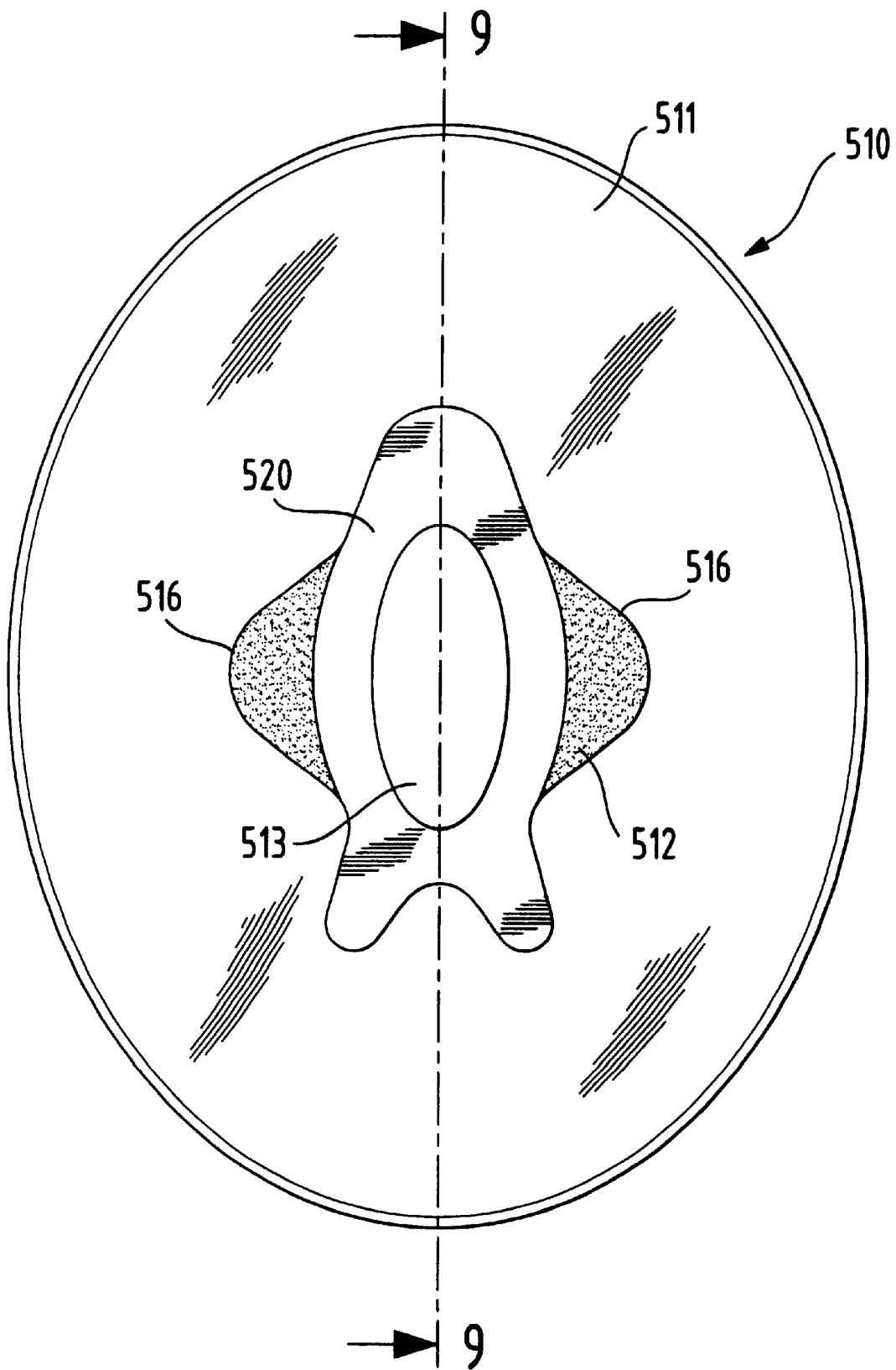

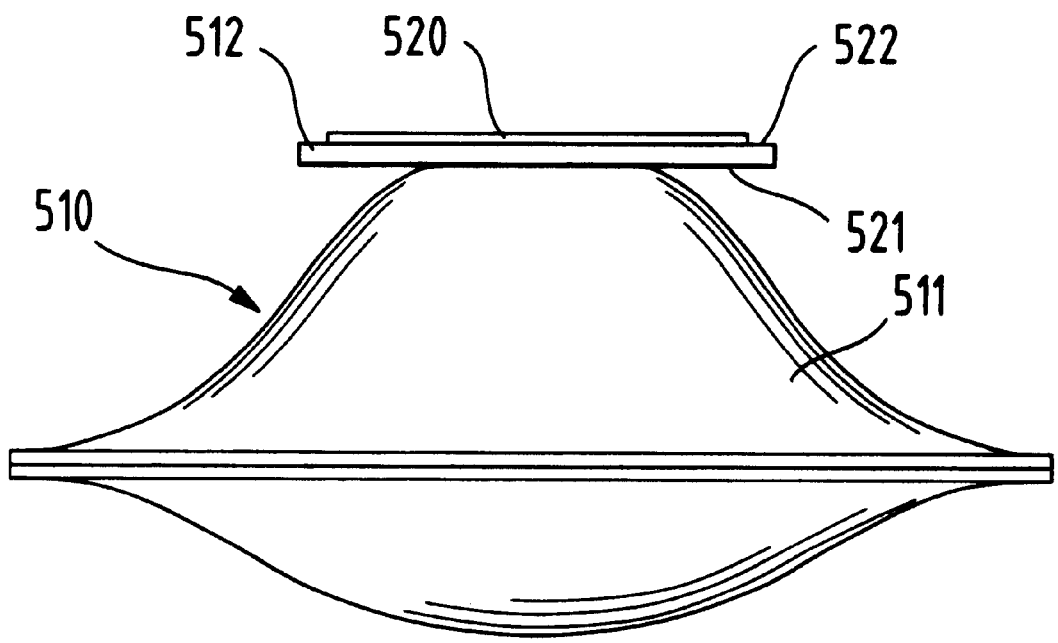
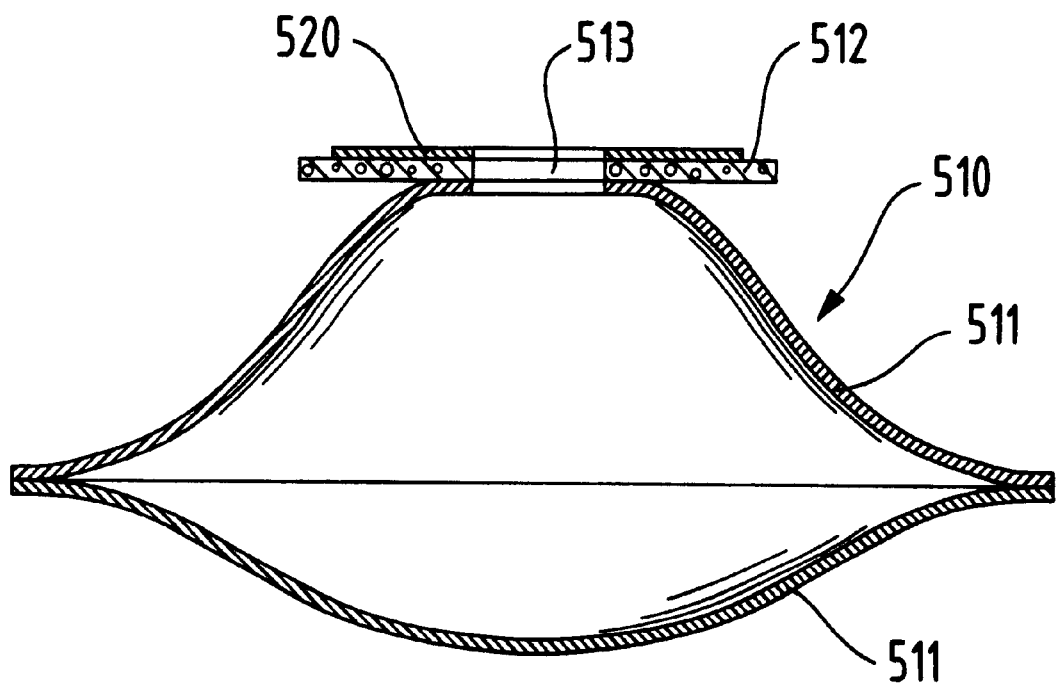

METHOD FOR COLLECTING AND DISPOSING OF HUMAN WASTE

FIELD OF THE INVENTION

This invention relates to a method for collecting and disposing of human waste, i.e., urine and feces, from an individual such as a baby, small child or an adult, wherein a disposable urine management device and a disposable fecal management device, are used independently and simultaneously.

BACKGROUND OF THE INVENTION

It has been known for many years to use disposable devices for collecting and disposing of human waste, in particular from babies and small children, as a domestic use typically, and from adults, both as a domestic and institutional use. Such known disposable devices are for the most part, disposable absorbent diapers equipped with fastening means to secure the diaper to the wearer, ready to wear disposable garments such as training pants, and disposable absorbent pads designed to be kept in place by reusable or disposable pants and panties.

In all these known configurations the disposable devices are designed to cope with both urine and feces, and are described as one-piece devices which cover the entire crotch area of the wearer, spanning the uro-genital and perineal areas.

Disposable diapers having specially designed features to cope with fecal material, both inside the diaper or by connection to an outside receptacle, are well known; however, in all such instances, the proposed diapers are destined to be used as a single implement to collect/dispose of both urine and fecal material and thus destined to cover the entire crotch area of the wearer.

The use of the known disposable absorbent devices of the type described above has, however, proven to create issues relating to skin irritation, due to the close contact to the skin of a relatively large piece of absorbent material and by the fact that the urine and/or feces discharged by the wearer are likely to be kept in contact with the skin of the wearer by the closely fitted absorbent device.

Furthermore, the known devices being constituted of a single article, no method is known in the art to cater independently to both the urine and fecal management needs of a baby, small child, or adult.

Individually, the use of disposable fecal management devices and disposable urine management devices are known. For example, disposable urine management devices are described in EP 0 140 470, WO 85/0328 and U.S. Pat. No. 4,804,377. Disposable fecal management devices are described in U.S. Pat. No. 3,577,989 and U.S. Pat. No. 4,784,656.

However, there is no suggestion from the above art to use disposable fecal management devices simultaneously with disposable urine management devices.

U.S. Pat. No. 2,920,625 and U.S. Pat. No. 4,200,102 describe reusable devices designed to cope with both urine and feces through the use of separate receptacles. Such devices are cumbersome, not disposable and cover the entire crotch area of the wearer.

It has now been discovered that the above issues can be overcome by the simultaneous and independent use of a disposable fecal management device and a disposable urine management device. Such a method of use allows greater flexibility as the devices can be used independently form one another.

BRIEF SUMMARY OF THE INVENTION

The invention is a method for collecting and disposing of urine and fecal excrement from an individual. The method is the simultaneous and independent use of a disposable urine management device and a disposable fecal management device. The disposable urine management device is independently applied in a releasable manner to the uro-genital area of the individual while the disposable fecal management device is independently applied in a releasable manner to the perineal area of the individual.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number.

FIG. 2 is a side view of the disposable urine management device of FIG. 1.

FIG. 3 is a cross-sectional view taken along line 3—3 of FIG. 1.

FIG. 4 is a plan view of another embodiment of a disposable urine management device of the present invention.

FIG. 5 is a cross-sectional view taken along line 5—5 of FIG. 4.

FIG. 6 is a cross-sectional view of another embodiment of a disposable urine management device of the present invention.

FIG. 7 is a plan view of a disposable fecal management device of the present invention.

FIG. 8 is side view of the disposable fecal management device of FIG. 7.

FIG. 9 is a cross-sectional view taken along line 9—9 of FIG. 7.

DETAILED DESCRIPTION OF THE INVENTION

Figure 1:
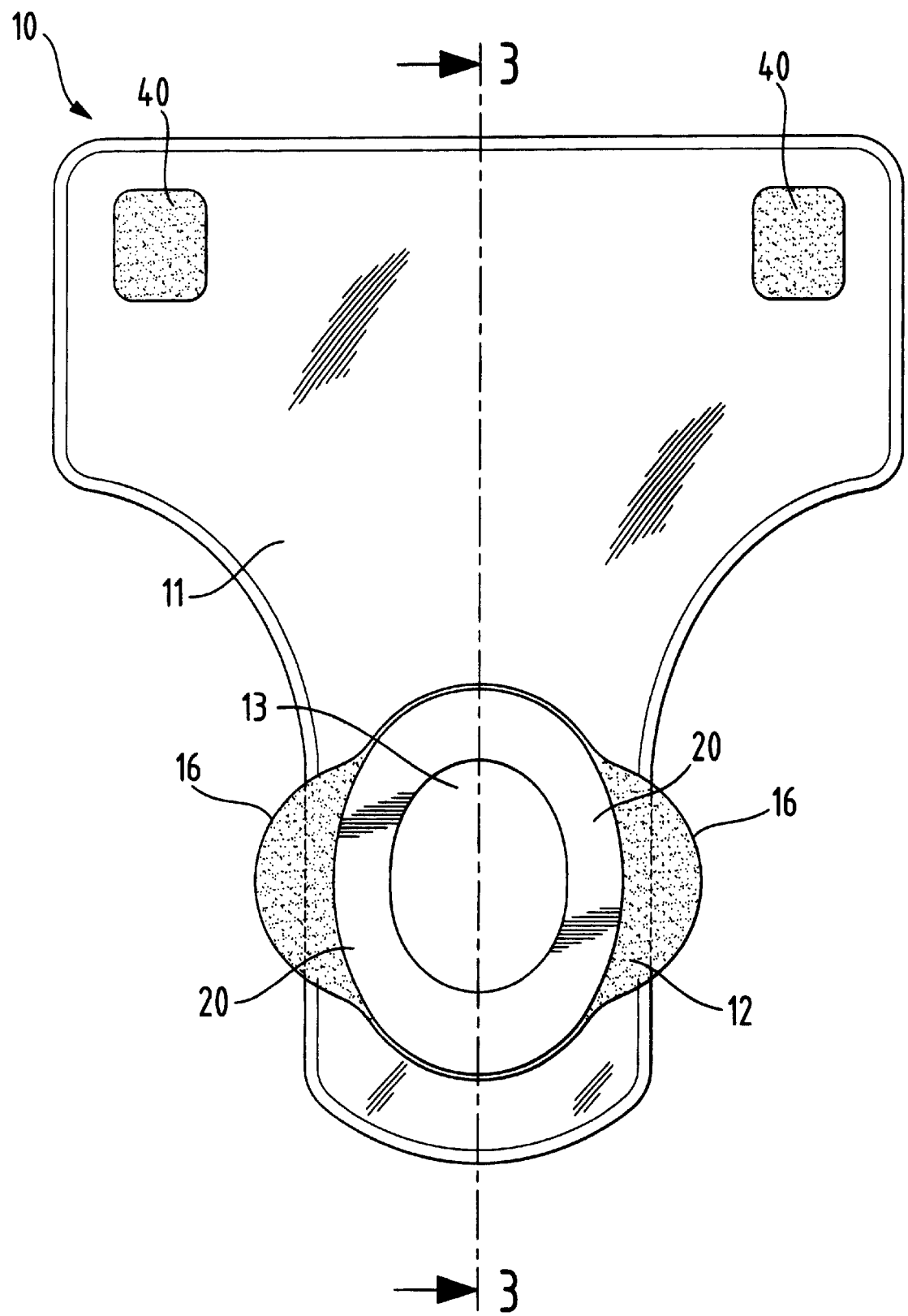
FIG. 1 is a plan view of a disposable urine management device of the present invention.

The term "disposable" as used herein describes devices which generally are not intended to be laundered or otherwise restored or reused (i.e., they are intended to be discarded after a single use and, preferably, to be recycled, composted or otherwise disposed of in an environmentally compatible manner).

Referring now to FIGS. 1–3, there is shown a disposable urine management device (10). Disposable urine management device (10) comprises a bag (11) having an aperture (13) and a flange (12) surrounding the aperture for adhesive attachment to the body of a wearer.

The bag (11) as used herein is a flexible receptacle for the containment of discharged urine. The bag (11) can be provided in any shape or size depending on the intended use thereof, i.e. whether the device is intended for bedridden patients or active patients suffering from incontinence. For example elongated bags which are principally tubular or rectangular are typically utilized by bedridden patients and elderly incontinence sufferers. For more active wearers whether infants or adults, the urine management device should preferably be anatomically shaped such that the device follows the contours of the body and can be worn inconspicuously by the wearer under normal garments.

Particularly, preferred shapes are cone shaped bags, truncated shaped bags and pyramidal or truncated pyramidal or cone shaped bags. In addition, the bag (11) is preferably shaped to fit the uro-genital region of the wearer to ensure good contact between the flange (12) and the skin of the wearer.

The bag (11) is preferably designed to provide sufficient volume for urine under a variety of wearing conditions, also when worn by a freely moving, i.e., not bedridden wearer.

The bag (11) is designed to safely contain any entrapped material, typically it will be liquid impermeable, yet it may be breathable. The bag is designed of sufficient strength to resist rupturing in use.

According to the present invention, depending on the shape of the bag (11) required, the bag may be made from a unitary piece of material or from a number of separate pieces of material, which may be identical or different and which are sealed at their respective peripheries.

According to the present invention the bag can comprise one or multiple layers, preferably two or three layers. The layer on the inside of the bag, which will typically at least partially come in contact with urine is called the inner layer. The outermost layer of the bag, which will typically at least partially come in contact with the skin of the wearer and the garments of the wearer, is called the outer layer.

The layers of the bag material may be provided from any material, so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film layer and two non-woven layers. In an even more preferred embodiment the film is interposed between the two non-woven layers. This sequence of layers results in a closed fibrous structure, which has a particularly pleasing sensation on contact with the skin of the wearer.

The non-woven layer or the non-woven layers comprised by the bag (11) may be hydrophobic or hydrophilic. For example, if the bag comprises a film layer, further non-woven layers may be hydrophilic or hydrophobic. If the bag does not comprise a film layer, preferably at least one non-woven layer is hydrophobic. It may even be desirable to make both non-woven layers hydrophobic to ensure that the bag is liquid impervious.

Typically, the non-woven layer is treated with a surface active material, such as a fluorochemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness. The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

As shown in FIG. 1 the bag (11) is provided with an aperture (13) whereby urine is received from the body prior to storage within the bag cavity. The aperture (13) is surrounded by a flange (12) and may be provided in any shape or size, such as circular, oblong, heart shaped and may be symmetrical or asymmetrical, preferably the aperture has an oblong configuration either in the longitudinal or in the transversal direction, most preferably the contours of the aperture are in the shape of two ellipses with the respective main axes being substantially perpendicular.

The flange (12) is attached to the bag (11) according to means known to the man skilled in the art, preferably adhesives.

The flange may be provided in any size depending on the wearer group for which the device is intended. Similarly the flange may be provided in any shape and preferably has a symmetrical, slightly oblong shape, preferably comprising a plurality of lobes.

The flange comprises a wearer facing surface (22) and an opposed garment facing surface (21). In a preferred embodiment these are two large, substantially flat surfaces.

The flange (12) should be made of soft, flexible and malleable material to allow easy placement of the flange to the uro-genital area. In addition, it is preferred that the flange (12) be made of a hydrophobic material such that if urine does come into contact with the perimeter (30) surrounding aperture (13) it is repelled and does not wick to the outer edge (32) of flange (12). It is also desirable to construct the flange (12) from a breathable material to avoid the problem of entrapment and condensation of moisture vapour given off by the body of the wearer and thus, the hot, clammy and uncomfortable conditions after a short period of use.

Suitable materials for the flange (12) include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

According to the present invention the wearer facing surface (22) of the flange (12) comprises a body-compatible adhesive (20). The adhesive (20) is preferably covered with a release means (not shown) in order to protect the adhesive layer prior to use, such as siliconized paper. The adhesive (20) can cover the entire wearer facing surface of the flange or more preferably have at least one, preferably two to six non-adhesive portions.

These portions may be adhesive free or may contain inactivated or covered adhesives. As is evident from FIG. 1, the adhesive (20) is in one preferred embodiment not applied to the entire wearer facing surface area of the flange (12), so as to provide lobes (16) on either side of the flange (12) which are non-adhesive and can thereby serve as placement lobes to facilitate placement and removal of the device whilst avoiding contact with the adhesive. These lobes are however preferably also covered by the release paper. Before application of the urine management device (10) to the skin of the wearer, the release means if present is removed.

According to the present invention any medically approved water resistant pressure sensitive adhesive may be used to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal are hydrophillic hydrogels formed from crosslinking polymers with a plastisicer to form a 3-dimensional matrix.

The adhesive (20) can be applied to the wearer facing surface (22) of the flange (12) by any means known in the art such as slot coating, spiral, or bead application or printing. Typically the adhesive is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example for urine management devices to be used for children the amount of adhesive may be less than for urine management devices designed for active adult incontinence sufferers.

Absorbent material (15) is contained within the bag (11). The absorbent material (15) may comprise any absorbent material which is capable of absorbing and retaining liquids such as urine. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material (15) may be positioned in the bag (11) in any suitable manner. For example, the absorbent material (15) may be loosely arranged within the bag (15) or may be secured to the inner layer of the bag (11). Any known techniques for securing absorbent material to nonwoven and film substrates may be used to secure the absorbent material (15) to the inner layer of the bag. The absorbent material may also be arranged to have any desired shape or configuration (e.g., rectangular, oval, circular, etc.).

In the embodiment shown in FIGS. 1–3, the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device. The adhesive (40) may be any medically approved water resistant pressure sensitive adhesive such as hydrocolloid adhesives and hydrogel adhesives. Particularly effective adhesives in providing the desired adhesive properties to secure the flange to the skin of the wearer whilst allowing for relatively painless application and removal are hydrophilic hydrogels formed from crosslinking polymers with a plastisicer to form a 3-dimensional matrix.

Referring now to FIGS. 4—5, there is shown another embodiment of a disposable urine management device (110). Disposable urine management device (110) comprises a bag (111) having an aperture (113), a flange (112) surrounding the aperture for adhesive attachment to the body of a wearer, and absorbent material (115) contained within the bag (111).

The flange (112) includes a raised, curved bulge (150) positioned beneath the aperture (113) and extending across the flange (112) for approximately the width of the aperture (113). The bulge (150) is shaped to span the perineum of an infant.

Referring now to FIG. 6, there is shown another embodiment of a disposable urine management device (210). Disposable urine management device (210) comprises a bag (211) having an aperture (213), a flange (212) surrounding the aperture for adhesive attachment to the body of a wearer and absorbent material (215) contained within the bag (211).

Disposable urine management device (210) also comprises an additional acquisition layer (270). Acquisition layer (270) is shown in FIG. 6 to be secured to the inner surface of bag (211). However, the acquisition layer (270) may also be secured to the flange (212), or both the flange (212) and the inner surface of bag (211). Acquisition layer (270) is preferably positioned such that it separates the genitalia of the wearer from coming into direct contact with the absorbent material (215). Acquisition layer (270) is fluid pervious allowing urine to readily pass through so that it may be absorbed by absorbent material (215).

The acquisition layer (270) may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wet-laid, meltblown, hydroentangled, or otherwise processed as is known in the art.

The acquisition layer (270) is designed to have a pore size such that the absorbent material (215) is not allowed to pass through and contact the wearer's skin. While designed not to have to large of a pore size which permits the passage of absorbent material (215), the acquisition layer (270) preferably has a pore size which is greater than the pore size of the absorbent material (215).

Preferably, the acquisition layer (270) is less hydrophilic than the absorbent material (215). The acquisition layer (270) may be treated with a surfactant to increase its initial wettability. When treated with surfactant, however, the acquisition layer (270) should still be less hydrophilic than the absorbent material (215). Suitable methods for treating the acquisition layer (270) with a surfactant include spraying the acquisition layer (270) with the surfactant and immersing the material into the surfactant. Alternatively, a surfactant may be incorporated into the acquisition layer (270).

Referring now to FIGS. 7–9, there is shown a disposable fecal management device (510). Disposable fecal management device (510) comprises a bag (511) having an aperture (513) and a flange (512) surrounding the aperture for adhesive attachment to the body of a wearer.

The bag (511) as used herein is a flexible receptacle for the containment of fecal excrement. The bag (511) can be provided in any shape or size depending on the intended use thereof, i.e. whether the device is intended for bedridden patients or active patients. For example elongated bags which are principally tubular or rectangular are typically utilized by bedridden patients and elderly incontinence sufferers. For more active wearers whether infants or adults, the fecal management device should preferably be anatomically shaped such that the device follows the contours of the body and can be worn inconspicuously by the wearer under normal garments.

Particularly, preferred shapes are flat circular type bags, rectangular shaped bags, cone shaped bags, truncated shaped bags and pyramidal or truncated pyramidal or cone shaped bags. In a most preferred embodiment of the present invention, the bag (511) has a flat circular shape. The bag (511) has a wearer facing portion and a garment facing portion where the wearer facing portion is disposed adjacent the buttocks of the wearer.

In addition, the bag (511) is preferably shaped to allow at least partial insertion and retention of the bag in-between the buttocks of the wearer and thereby ensure good contact between the flange and the skin of the wearer.

The bag (511) is preferably designed to provide sufficient volume for feces under a variety of wearing conditions, also when worn by a freely moving, i.e., not bedridden wearer. Sitting on the bag, for example, will result in a largely reduced volume is some portions of the bag. Thus, the bag is preferably shaped to provide sufficient volume in portions which are not subjected to much pressure in wearing conditions such as sitting.

The bag (511) is designed to safely contain any entrapped material, typically it will be liquid impermeable, yet it may be breathable. The bag is designed of sufficient strength to resist rupturing in use.

According to the present invention, depending on the shape of the bag (511) required, the bag may be made from a unitary piece of material or from a number of separate pieces of material, which may be identical or different and which are sealed at their respective peripheries.

According to the present invention the bag can comprise one or multiple layers, preferably two or three layers. The layer on the inside of the bag, which will typically at least partially come in contact with fecal material is called the inner layer. The outermost layer of the bag, which will typically at least partially come in contact with the skin of the wearer and the garments of the wearer, is called the outer layer.

The layers of the bag material may be provided from any material, so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (511) comprises three layers, preferably one film layer and two non-woven layers. In an even more preferred embodiment the film is interposed between the two non-woven layers. This sequence of layers results in a closed fibrous structure, which has a particularly pleasing sensation on contact with the skin of the wearer.

The non-woven layer or the non-woven layers comprised by the bag (511) may be hydrophobic or hydrophilic. For example, if the bag comprises a film layer, further non-woven layers may be hydrophilic or hydrophobic. If the bag does not comprise a film layer, preferably at least one non-woven layer is hydrophobic. It may even be desirable to make both non-woven layers hydrophobic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness. The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

The bag (511) is provided with an aperture (513) whereby feces is received from the body prior to storage within the bag cavity. The aperture (513) is surrounded by a flange (512) and may be provided in any shape or size, such as circular, oblong, heart shaped and may be symmetrical or asymmetrical, preferably the aperture has an oblong configuration either in the longitudinal or in the transversal direction, most preferably the contours of the aperture are in the shape of two ellipses with the respective main axes being substantially perpendicular.

The flange (512) is attached to the bag (511) according to means known to the man skilled in the art, preferably adhesives.

The flange may be provided in any size depending on the wearer group for which the device is intended. Similarly the flange may be provided in any shape and preferably has a symmetrical, slightly oblong shape, preferably comprising a plurality of lobes.

The flange comprises a wearer facing surface (522) and an opposed garment facing surface (521). In a preferred embodiment these are two large, substantially flat surfaces, however, the flange may also comprise projections designed to fit the perineal or coccygeal area of the wearer. For example, the flange (512) may include a raised, curved bulge (550) similar to the raised, curved bulge (150) illustrated in FIGS. 4 and 5.

The flange (512) should be made of soft, flexible and malleable material to allow easy placement of the flange to the uro-genital area. In addition, it is also preferred that the flange (512) be made of a hydrophobic, breathable material.

Suitable materials for the flange (512) include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

According to the present invention the wearer facing surface (522) of the flange (512) comprises a body-compatible adhesive (520). The adhesive (520) is preferably covered with a release means (not shown) in order to protect the adhesive layer prior to use, such as siliconized paper. The adhesive (520) can cover the entire wearer facing surface of the flange or more preferably have at least one, preferably two to six non-adhesive portions. These portions may be adhesive free or may contain inactivated or covered adhesives. As is evident from FIG. 8, the adhesive (520) is in one preferred embodiment not applied to the entire wearer facing surface area of the flange (512), so as to provide lobes (516) on either side of the flange (512) which are non-adhesive and can thereby serve as placement lobes to facilitate placement and removal of the device whilst avoiding contact with the adhesive. These lobes are however preferably also covered by the release paper. Before application of the fecal management device (510) to the skin of the wearer, the release means if present is removed.

According to the present invention any medically approved water resistant pressure sensitive adhesive may be used to attach the device to the perineal area of the wearer, such as hydrocolloid adhesives and hydrogel adhesives. Particularly effective adhesives in providing the desired adhesive properties to secure the flange to the skin of the wearer at the sensitive perineal area, whilst allowing for relatively painless application and removal are hydrophilic hydrogels formed from crosslinking polymers with a plasticiser to form a 3-dimensional matrix.

The adhesive (520) can be applied to the wearer facing surface (522) of the flange (512) by any means known in the art such as slot coating, spiral, or bead application or printing. Typically the adhesive is applied at a basis weight of from 20 $g/m^2$ to 2500 $g/m^2$, more preferably from 500 $g/m^2$ to 2000 $g/m^2$ most preferably from 700 $g/m^2$ to 1500 $g/m^2$ depending on the end use envisioned. For example for fecal management devices to be used for children the amount of adhesive may be less than for fecal management devices designed for adults.

Because the space between the uro-genital area and the perineal area of the wearer can be quite small, especially on infants and children, the respective flanges of the disposable urine management device and the disposable fecal management device need to be designed to cooperate with one another. If designed independently, the respective flanges may not make a good seal with the wearer's skin leading to the leakage of urine or fecal material. Examples of such independent designs are where the respective flanges overlap one another such that one of the flanges does not make a complete seal with the wearer's skin.

Other suitable designs for the disposable urine management device and the disposable fecal management device include those where one or both of the devices is held in place with the use of a separate mechanism. Examples of such separate mechanisms include but are not limited to pants, both disposable and reusable, and disposable absorbent articles, such as disposable diapers. When the disposable urine management device and the disposable fecal management device are held in place via a separate mechanism, they may or may not also include additional mechanisms to hold them in place such as the flanges described above.

While the present invention has been illustrated using the above designs for the disposable urine management device and the disposable fecal management device, the present invention is not limited to such designs. Accordingly, other suitable designs are also within the scope of the present invention. The particular design of the respective devices is not critical to carry out the present invention as long as each device is disposable, can be independently applied in a releasable manner to the respective regions of the individual, i.e., the uro-genital region and the perineal region, and can receive and contain the discharged exudates.

The method of use of the present invention is the simultaneous and independent use of the aforementioned disposable urine management device with the disposable fecal management device. The disposable urine management device is secured to the uro-genital area of the wearer for the collection of urine and the disposable fecal management device is secured to the perineal area of the wearer for the collection of feces. By independently collecting urine and feces in separate devices, the method of the present invention provides an improved efficiency over prior art one-pieces devices designed to collect both urine and feces. The prior art one-piece devices may need to be changed once the device has been loaded with either feces or urine. This is often inefficient as the one-piece device has not permitted to reach its full potential in holding both urine and feces due to the presence of one and not the other which stimulates a change.

In contrast, the method of the present invention allows each device to be changed independently such the each device may be used to its full extent. For example, if the urine management device becomes loaded with urine and the fecal management device is empty, only the urine management device needs to be changed. Alternatively, if the fecal management device becomes loaded with feces and the urine management device is empty, only the fecal management device needs to be changed.

Preferably the urine management device and the fecal management device are packaged together to form a kit for collecting and disposing of urine and fecal excrement from an individual. The equal number of urine management devices and fecal management devices may be packaged in the same kit. Alternatively, a different number of urine management devices and fecal management devices may be packaged in the same kit. Preferably, the kit will contain more urine management devices than fecal management devices.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for collecting and disposing of urine and fecal excrement from an individual comprising the steps of:

a) applying a disposable urine management device in a releasable manner to the uro-genital region of an individual; and b) applying a disposable fecal management device in a releasable manner to the perineal region of said individual;

wherein said urine management device and said fecal management device may be independently applied and in any sequence.

2. The method of claim 1 wherein each device includes a liquid impermeable bag wherein each of said bags has an aperture, said apertures being surrounded by an adhesively-faced flange for releasable attachment to the uro-genital and perineal areas of said individual, wherein said flanges are comprised of a breathable material.

3. The method of claim 2 wherein each of said bags is breathable.

4. The method of claim 2 wherein each of said bags comprises at least one layer.

5. The method of claim 4 wherein each of said bags comprises at least one inside layer and an outside layer.

6. The method of claim 5 wherein said outside layer comprises a non-woven layer.

7. The method of claim 6 wherein said non-woven layer is impregnated with a lotion.

8. The method of claim 2 wherein the bag of said disposable urine management device comprises an absorbent material.

9. The method of claim 8 wherein said absorbent material is selected from the group consisting of comminuted wood pulp; creped cellulose wadding; meltblown polymers; chemically stiffened, modified or cross-linked cellulosic fibers; tissue; absorbent foams; absorbent sponges; super-absorbent polymers; and absorbent gelling materials.

10. The method of claim 2 wherein said disposable urine management device comprises an acquisition layer.

11. The method of claim 2 wherein at least one of said flanges comprises a raised, curved bulge.

12. A kit for collecting and disposing of urine and fecal excrement from an individual, said kit comprising a disposable urine management device and a disposable fecal management device.

* * * * *